US012453629B2

(12) United States Patent
Yang

(10) Patent No.: US 12,453,629 B2
(45) Date of Patent: Oct. 28, 2025

(54) SURGICAL VALVE AND IMPLANTATION DEVICE THEREFOR

(71) Applicant: SHANGHAI CINGULAR BIOTECH CORPORATION, Pudong (CN)

(72) Inventor: Jun Yang, Shanghai (CN)

(73) Assignee: SHANGHAI CINGULAR BIOTECH CORPORATION, Pudong (CN)

(*) Notice: Subject to any disclaimer, the term of this patent is extended or adjusted under 35 U.S.C. 154(b) by 559 days.

(21) Appl. No.: 17/439,780

(22) PCT Filed: Mar. 17, 2020

(86) PCT No.: PCT/CN2020/079611

§ 371 (c)(1),
(2) Date: Sep. 15, 2021

(87) PCT Pub. No.: WO2020/187196

PCT Pub. Date: Sep. 24, 2020

(65) Prior Publication Data

US 2022/0183829 A1 Jun. 16, 2022

(30) Foreign Application Priority Data

Mar. 19, 2019 (CN) ........................ 201910209795.X

(51) Int. Cl.
*A61F 2/24* (2006.01)

(52) U.S. Cl.
CPC .......... *A61F 2/2418* (2013.01); *A61F 2/2427* (2013.01); *A61F 2/2433* (2013.01); *A61F 2220/0016* (2013.01)

(58) Field of Classification Search
CPC ........ A61F 2/24; A61F 2/2418; A61F 2/2427; A61F 2220/0016; A61F 2/00; A61F 2/02;
(Continued)

(56) References Cited

U.S. PATENT DOCUMENTS 5,295,977 A * 3/1994 Cohen ............... A61M 25/0606 604/164.12
5,643,209 A * 7/1997 Fugoso ............... A61M 25/008 604/103

(Continued)

FOREIGN PATENT DOCUMENTS

CN 1745727 A 3/2006
CN 101180010 A 5/2008

(Continued)

OTHER PUBLICATIONS

Definition; "Telescope." Merriam-Webster.com Dictionary, Merriam-Webster, https://www.merriam-webster.com/dictionary/telescope. Accessed Mar. 8, 2024.4 (Year: 2024).*

(Continued)

*Primary Examiner* — Jerrah Edwards
*Assistant Examiner* — Jose H. Trevino, III
(74) *Attorney, Agent, or Firm* — David S. Bradin; Maynard Nexsen PC

(57) ABSTRACT

Provided are a surgical valve and an implantation device therefor. The surgical valve includes a valve body and an expandable stent. The valve body includes a valve base and a valve frame disposed on the valve base. The expandable stent is of a cylindrical structure with openings at a first end and a second end of the expandable stent. The first end of the expandable stent is sleeved on the valve body, and a plurality of insertion hooks configured to be inserted into a native valve annulus are disposed along a periphery of the first end of the expandable stent. The second end of the expandable stent is configured to expand radially to be supported on one side of the native valve annulus.

7 Claims, 4 Drawing Sheets

(58) Field of Classification Search
CPC ...... A61F 2/2412; A61F 2/243; A61F 2/2433; A61F 2/2439; A61F 2/848; A61F 2002/8483; A61F 2002/8486; A61F 2/82; A61F 2/958; A61F 2002/9583; A61F 2/9522; A61F 2/9517; A61F 2/95; A61F 2/2466; A61F 2/2463
See application file for complete search history.

(56) References Cited

U.S. PATENT DOCUMENTS

| | | | | |
|---|---|---|---|---|
| 6,007,557 | A * | 12/1999 | Ambrisco | A61F 2/011 606/159 |
| 2012/0010699 | A1* | 1/2012 | Vesely | A61F 2/2418 623/2.11 |
| 2012/0020699 | A1* | 1/2012 | Kamimura | G03G 15/0813 399/119 |
| 2012/0078357 | A1* | 3/2012 | Conklin | A61F 2/2412 623/2.18 |
| 2016/0074163 | A1 | 3/2016 | Yang et al. | |
| 2017/0231765 | A1* | 8/2017 | Desrosiers | A61F 2/2436 623/2.11 |
| 2020/0352706 | A1 | 11/2020 | Campbell | |

FOREIGN PATENT DOCUMENTS

| | | | |
|---|---|---|---|
| CN | 101291637 | A | 10/2008 |
| CN | 102256568 | A | 11/2011 |
| CN | 102458309 | A | 5/2012 |
| CN | 103200900 | A | 7/2013 |
| CN | 103889369 | A | 6/2014 |
| CN | 103974674 | A | 8/2014 |
| CN | 104055602 | A | 9/2014 |
| CN | 104427956 | A | 3/2015 |
| CN | 104602646 | A | 5/2015 |
| CN | 105142578 | A | 12/2015 |
| CN | 105263442 | A | 1/2016 |
| CN | 106456324 | A | 2/2017 |
| CN | 107233146 | A | 10/2017 |
| CN | 107405197 | A | 11/2017 |
| CN | 108135592 | A | 6/2018 |
| CN | 109938879 | A | 6/2019 |
| CN | 210250166 | U | 4/2020 |

OTHER PUBLICATIONS

Chinese-language International Search Report and Written Opinion issued in counterpart PCT Application No. PCT/US2020/028622 dated May 28, 2020, along with English translation (twelve (12) pages).
Chinese First Office Action issued in counterpart CN Application No. 201910209795.X dated Aug. 11, 2020, with English translation.
Chinese Second Office Action issued in counterpart CN Application No. 201910209795.X dated Apr. 6, 2021, with English translation.
Chinese Supplementary Search of CN prior application.

* cited by examiner

SURGICAL VALVE AND IMPLANTATION DEVICE THEREFOR

CROSS REFERENCE TO RELATED APPLICATIONS

This is a national stage application filed under 37 U.S.C. 371 based on International Patent Application No. PCT/CN2020/079611, filed Mar. 17, 2020, which claims priority to Chinese Patent Application No. 201910209795.X filed with the China National Intellectual Property Administration (CNIPA) on Mar. 19, 2019, the disclosures of which are incorporated herein by reference in their entireties.

TECHNICAL FIELD

The present application relates to the technical field of medical equipments and, in particular, to a surgical valve and an implantation device therefor.

BACKGROUND

A surgical valve is common medical equipment for the treatment of valvular heart disease, primarily for the replacement of a native valve that has severe lesions and cannot be repaired. The surgical valve includes two types, mechanical valve and biological valve, which are selected according to body conditions and needs of patients. Compared with an invasive valve, the surgical valve has a wider range of applications, lower application requirements for patients, longer product service life, and more economical surgical costs. Therefore, the surgical valve stably occupies a place in the market of treatment products for valvular heart disease.

The surgical valve needs to replace an diseased native valve through surgical procedures to achieve the purpose of treatment. The surgery usually needs equipment to open the thorax first, and then the heart valve is exposed. After lesions are cleared, the surgical valve is sewed at the position of a native valve annulus so as to be fixed. However, because the sewing process is relatively complicated and the surgery time is relatively long, the risk of the surgery is increased.

SUMMARY

The present application provides a surgical valve and an implantation device therefor, so as to solve the problem that the risk of damage and failure of the surgical valve is high and the time of surgery is relatively long due to the fact that the surgical valve needs to be sewed in the related art. Therefore, surgical procedures are more simple, and a valve body and a native valve annulus are combined more closely, thereby reducing the risk of the valve body falling off in the human body after the surgery.

The present application provides the surgical valve including the valve body and an expandable stent. The valve body includes a valve base and a valve frame disposed on the valve base. The expandable stent is of a cylindrical structure with openings at two ends. One end of the expandable stent is sleeved on the valve base, and the expandable stent is provided with a plurality of insertion hooks configured to be inserted into a native valve annulus and disposed along a periphery of the one end of the expandable stent. Another end of the expandable stent is configured to be radially expanded so as to be supported on one side of the native valve annulus.

The present application also provides an implantation device for the surgical valve including a fixing member and an expanding structure. The fixing member is configured to detachably disposed on the valve body. The expanding structure is configured to pass through the valve body to be located within the expandable stent and is configured to radially expand another end of the expandable stent to a preset position.

REFERENCE LIST

Figure 1:
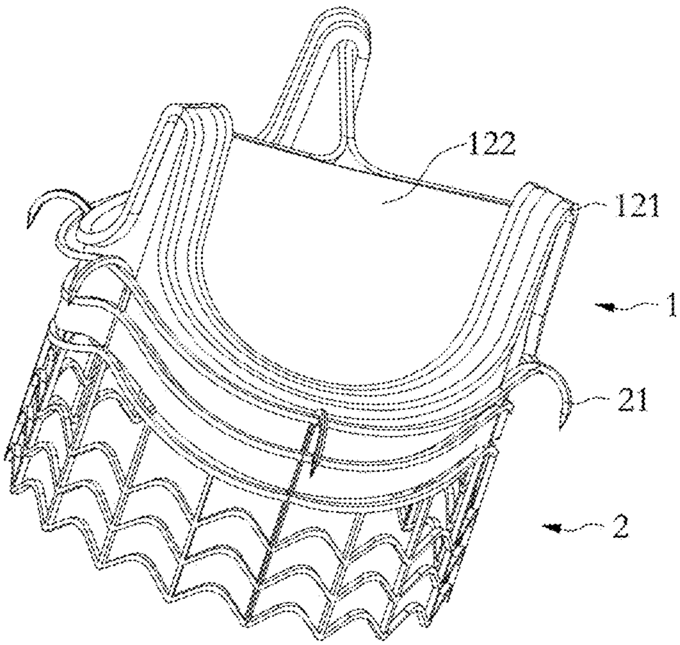
FIG. 1 is a structural view of a surgical valve according to an embodiment of the present application.

1 valve body
11 valve base
12 valve frame
121 support frame
122 valve leaflet
2 expandable stent
21 insertion hook
3 fixing member
301 first hole
302 second stepped surface
303 second hole
31 valve holder
311 perforated connector
312 support arm
4 push-pull member
401 first stepped surface
41 first portion
42 second portion
5 expansion assembly
51 telescopic arm
511 first arm
512 second arm

DETAILED DESCRIPTION

The technical solutions of the present application are described hereinafter through embodiments in conjunction with the drawings. The embodiments described herein are merely intended to explain, and not to limit, the present application. For ease of description, only part, not all, of parts related to the present application are illustrated in the drawings.

In the description of the present application, unless otherwise specified and limited, the term "connected to each other", "connected" or "fixed" is to be construed in a broad sense, for example, as fixedly connected, detachably connected, or integrated; mechanically connected or electrically connected; directly connected to each other or indirectly connected to each other via an intermediary; or internally connected between two elements or interactional between two elements. Meanings of the preceding terms in the present application may be understood according to situations.

In the present application, unless otherwise specified and limited, when a first feature is described as "on" or "below" a second feature, the first feature and the second feature may be in direct contact or be in contact via another feature between the two features instead of being in direct contact. Moreover, when the first feature is described as "on", "above" or "over" the second feature, the first feature is right on, above or over the second feature or the first feature is obliquely on, above or over the second feature, or the first feature is simply at a higher level than the second feature. When the first feature is described as "under", "below" or "underneath" the second feature, the first feature is right under, below or underneath the second feature or the first feature is obliquely under, below or underneath the second feature, or the first feature is simply at a lower level than the second feature.

In the description of this embodiment, the orientations or position relations indicated by terms such as "above", "below", and "right" are based on orientations or position relations shown in the drawings. These orientations or position relations are intended only to facilitate and simplify description of the present application, and not to indicate or imply that a device or element referred to must have such specific orientations or must be configured or operated in such specific orientations. Thus, these orientations or position relations are not to be construed as limiting the present application. In addition, the terms "first" and "second" are used only to distinguish between descriptions and have no special meaning.

Figure 2:
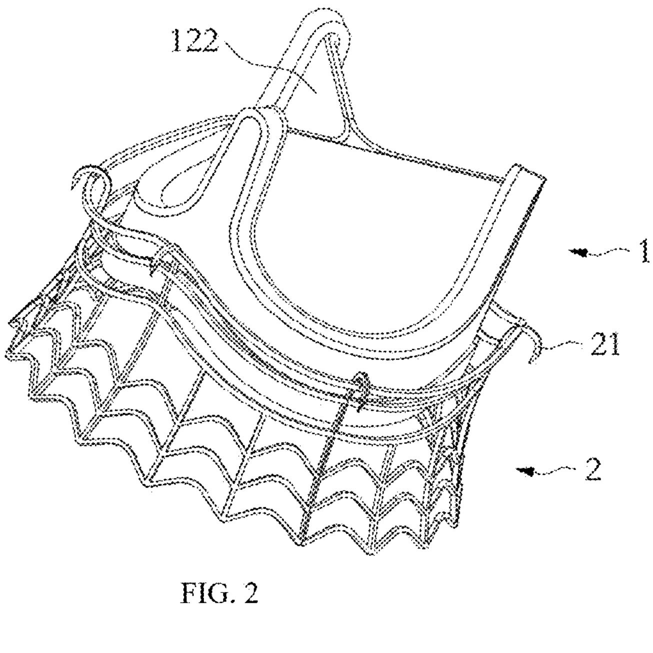
FIG. 2 is a structural view of another surgical valve (in an operating state) according to an embodiment of the present application.
Figure 3:
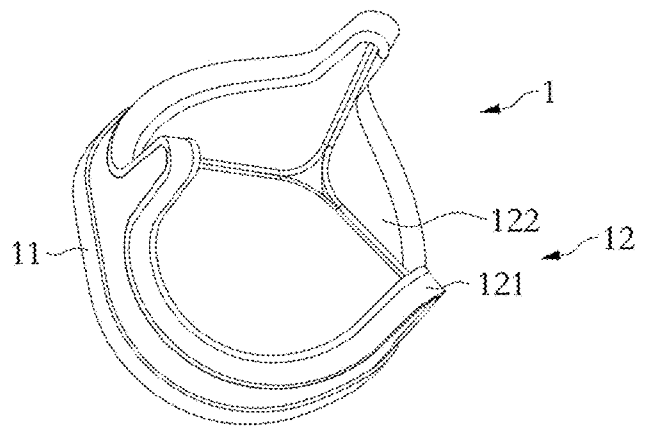
FIG. 3 is a structural view of a valve body according to an embodiment of the present application.

FIG. 1 is a structural view of a surgical valve according to an embodiment of the present application; FIG. 2 is a structural view of another surgical valve (in an operating state) according to an embodiment of the present application; and FIG. 3 is a structural view of a valve body according to an embodiment of the present application. As shown in FIGS. 1 and 2, the surgical valve provided in this embodiment includes a valve body 1 and an expandable stent 2. As shown in FIG. 3, the valve body 1 includes a valve base 11 and a valve frame 12. The valve frame 12 includes a support frame 121. Three valve leaflets 122 are mounted on the support frame 121, and the three valve leaflets 122 can be opened or closed simultaneously. When the three valve leaflets 122 are opened simultaneously, a channel is formed for blood to flow through; when the three leaflets 122 are closed simultaneously, the blood can be blocked from flowing through. The valve body 1 is a main structure of the surgical valve in the related art and is not repeated herein.

The expandable stent 2 is of a cylindrical structure with openings at two ends, and one end of the expandable stent 2 is sleeved on the valve base 11. The expandable stent 2 is provided with a plurality of insertion hooks 21 (as shown in FIG. 1) configured to be inserted into a native valve annulus and disposed along a periphery of the one end of the expandable stent 2. The number of insertion hooks 21 is not limited and can be set according to situations. Another end of the expandable stent 2 is capable of being expanded radially under the action of an external force and supported on one side of the native valve annulus. In this embodiment, a diameter of the intermediate portion of the expandable stent 2 is fixed, and the diameter of the intermediate portion of the expandable stent 2 is less than or equal to diameters of the two ends of the expandable stent 2, that is, the intermediate portion cannot be expanded and contracted. The two ends of the expandable stent 2 can be radially expanded, with certain elasticity and expandability, so that the expandable stent 2 is conveniently mounted on the valve base 11, and an end of the expandable stent 2 farther away from the valve base 11 is capable of being supported on one side of the native valve annulus.

In this embodiment, the expandable stent 2 is of a reticular structure and made of a non-memory metal (such as stainless steel or cobalt-chromium alloy), so the strength and stability of the expandable stent 2 can be enhanced. Moreover, an end of the expandable stent 2 farther away from the valve body 1 can be ensured to always remain in an expanded state after being expanded radially, so as to cooperate with the insertion hook 21 to fix the valve body 1 at the position of the native valve annulus. The reticular structure is coated with a biocompatible fabric or a biological tissue material, such as a polyester fabric, a composite fabric having polyester, a pericardial tissue of cattle, pigs or other animals, and the like. The reticular structure includes a plurality of vertical lines arranged in a cylindrical structure and horizontal lines disposed between adjacent vertical lines. In this embodiment, the horizontal lines are curved lines in order to conveniently expand the expandable stent 2. The insertion hook 21 and the expandable stent 2 are integrated. The insertion hook 21 is formed by bending of a vertical line which constitutes of the reticular structure and stretches out of the reticular structure. An end portion of the insertion hook 21 is designed as a cone structure. Moreover, in order to improve the fixing effect of the insertion hook 21, the insertion hook 21 is further provided with a barbed structure, such as a barb and a hook, so that the insertion hook 21 is conveniently inserted into the native valve annulus to fix the valve body 1. In other embodiments, the insertion hook 21 may be disposed separate from the expandable stent 2, and the insertion hook 21 is fixed to the expandable stent 2 in a manner of welding or the like.

In this embodiment, the limitation on the expandable stent 2 is not limited thereto. The expandable stent 2 may also be of a self-expanding structure. The expandable stent 2 is of a reticular structure, made of a memory metal (for example, a nickle-titanium alloy), and is bound and fixed in a cylindrical shape having a diameter not less than that of the valve body 1. When the expandable stent 2 is delivered to the position of the native valve annulus, the expandable stent 2 self-expands after being released from external fixation. The diameter of the self-expanded expandable stent 2 is slightly greater than a diameter of the middle opening of the native valve annulus, so that the valve body 1 is fixed at the position of the native valve annulus.

A plurality of insertion hooks 21 cooperate with the end of the expandable stent 2 farther away from the valve body 1 so that the valve body 1 can be fixed at the position of the native valve annulus. When the surgical valve is fixed, the insertion hook 21 is capable of being inserted into the native valve annulus, and then the end of the expandable stent 2 farther away from the valve body 1 is expanded and supported on one side of the native valve annulus (as shown in FIG. 2). The valve body 1 is fixed at the position of the native valve annulus from two sides of the native valve annulus. Compared with the related art, this embodiment omits the process of sewing the valve body 1 to the position of the native valve annulus, and the valve body 1 can be more firmly combined at the position of the native valve annulus. Therefore, the damage to the valve body 1 during the sewing process can be avoided, the surgery time can be shortened, the risk of the surgery can be reduced, and the risk of the valve body falling off in the human body after the surgery can also be avoided.

Figure 4:
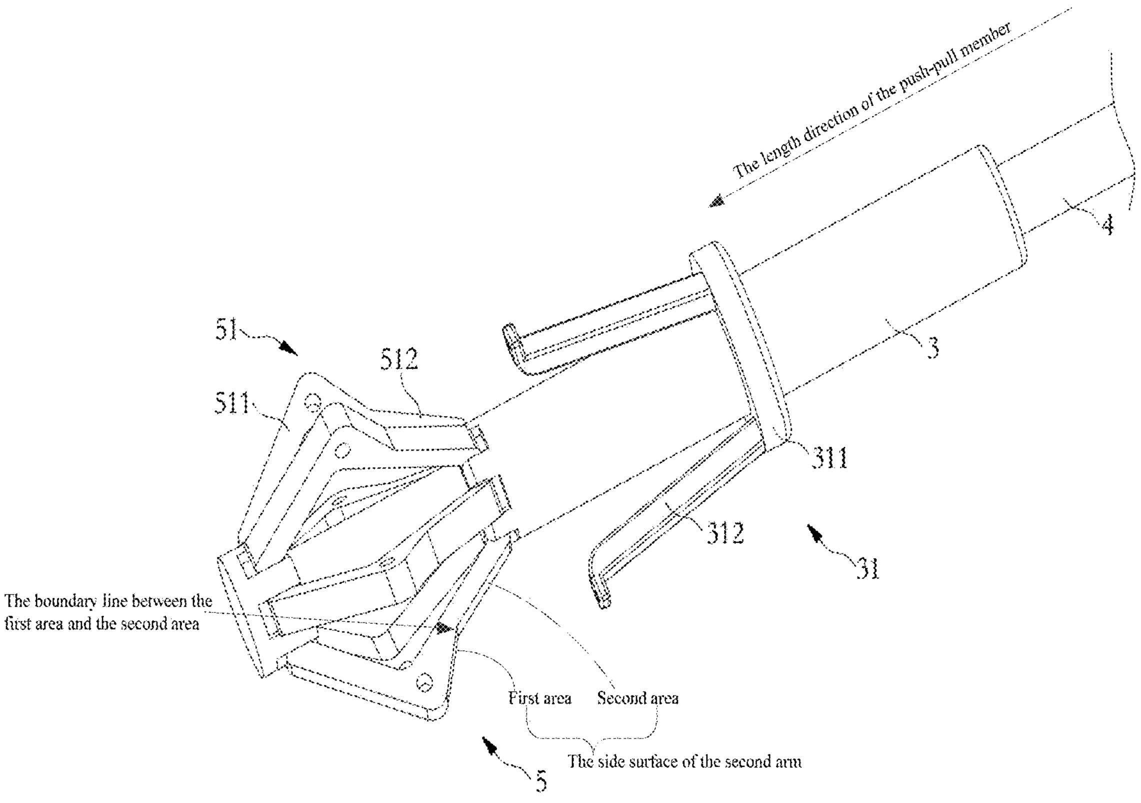
FIG. 4 is a structural view of an implantation device for a surgical valve according to an embodiment of the present application.
Figure 5:
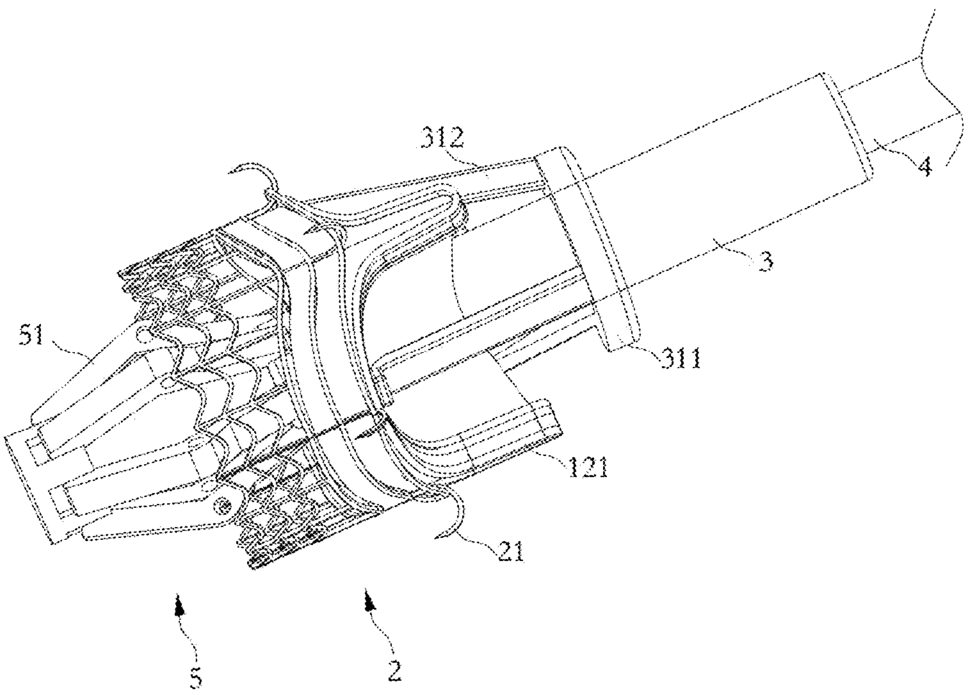
FIG. 5 is a view of an implantation device for a surgical valve in an operating state according to an embodiment of the present application.
Figure 6:
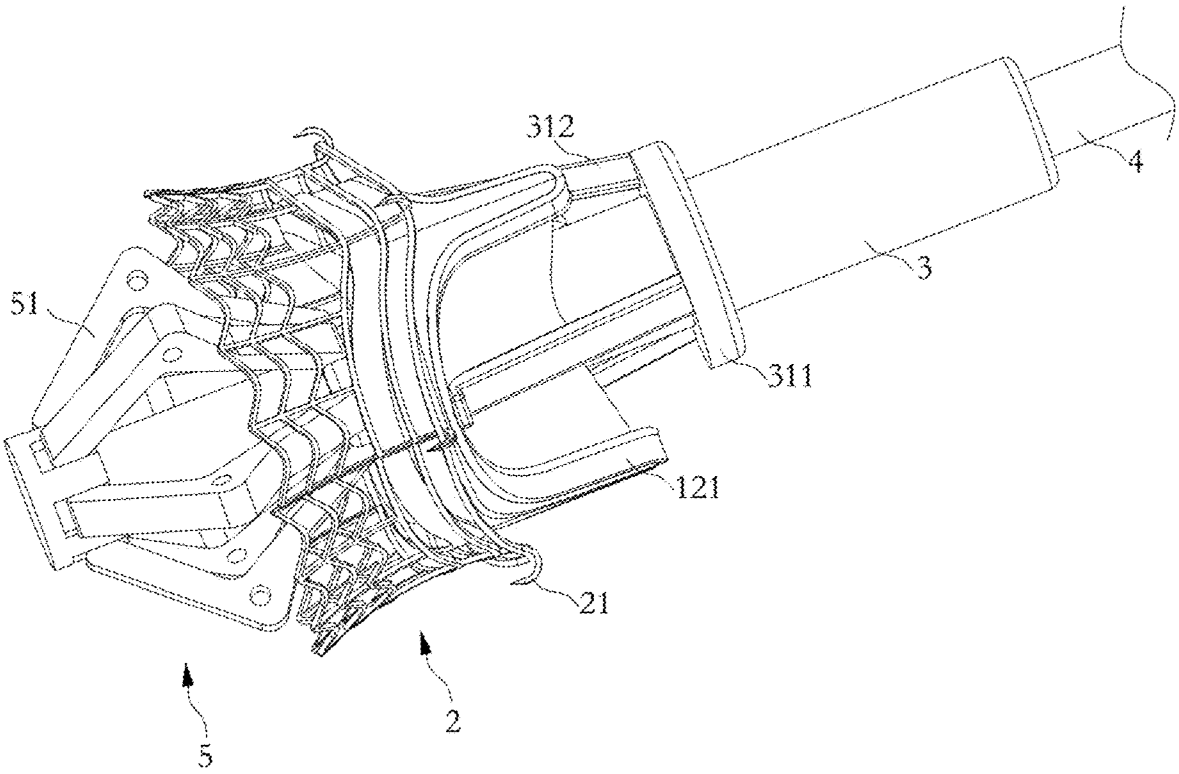
FIG. 6 is a view of another implantation device for a surgical valve in an operating state according to an embodiment of the present application.

This embodiment also provides an implantation device for the surgical valve. FIG. 4 is a structural view of an implantation device for a surgical valve according to an embodiment of the present application; FIG. 5 is a view of an implantation device for a surgical valve in an operating state according to an embodiment of the present application; and FIG. 6 is a view of another implantation device for a surgical valve in an operating state according to an embodiment of the present application. As shown in FIGS. 4 to 6, the implantation device for the surgical valve provided in this embodiment is configured to detachably penetrate the channel formed when the three valve leaflets 122 are simultaneously opened. Moreover, the implantation device is capable of expanding another end of the expandable stent 2 along the radial direction of another end of the expandable stent 2 to a preset position. The preset position refers to that another end of the expandable stent 2 is just supported on another side of the native valve annulus.

The implantation device includes a fixing member 3 and an expanding structure. The fixing member 3 is configured to penetrate a hole channel formed when the three valve leaflets 122 of the surgical valve are relatively opened, and the valve body 1 is detachably connected to the fixing member 3. In this embodiment, the fixing member 3 is of a cylindrical structure with openings at two ends. In other embodiments, the fixing member 3 may also be of a square cylindrical structure. The expansion structure also passes through the channel formed when the three valve leaflets 122 are simultaneously opened and is located within the expandable stent 2, and the expansion structure is capable of expanding the end of the expandable stent 2 farther away from the valve body 1 along the radial direction of the end of the expandable stent 2 to the preset position.

In this embodiment, the expansion structure includes a push-pull member 4 and an expansion assembly 5. The push-pull member 4 is configured to penetrate the fixing member 3, and each of two ends of the push-pull member 4 extend out of the fixing member 3. In this embodiment, the push-pull member 4 is of a cylindrical structure cooperating with the fixing member 3. The push-pull member 4 can be ensured to be capable of moving stably along the axial direction of the fixing member 3 during the push-pull process of the push-pull member 4 relative to the fixing member 3, and the shaking of the push-pull member 4 is avoided during the push-pull process. In other embodiments, the push-pull member 4 may also be a square column. In this case, the fixing member 3 is of a square cylindrical structure. An end of the expansion assembly 5 is connected to an end of the push-pull member 4, and another end of the expansion assembly 5 is connected to the fixing member 3. Under the driving of the push-pull member 4, the expansion assembly 5 is capable of expanding outwards along the radial direction of the expandable stent 2, so that the end of the expandable stent 2 farther away from the valve body 1 is expanded along the radial direction of the end of the expandable stent 2. Furthermore, under the driving of the push-pull member 4, the expansion assembly 5 is capable of being contracted inwards along the radial direction of the expandable stent 2.

The expansion assembly 5 includes a plurality of telescopic arms 51 disposed along a periphery of the push-pull member 4. An end of the telescopic arm 51 is connected to an end of the push-pull member 4, and another end of the telescopic arm 51 is connected to the fixing member 3. In this embodiment, the telescopic arm 51 includes a first arm 511 and a second arm 512 which are rotatably connected to each other. An end of the first arm 511 farther away from the second arm 512 is connected to the push-pull member 4, and an end of the second arm 512 farther away from the first arm 511 is connected to the fixing member 3. The angle between the extension direction of the first arm 511 and the axial direction of the push-pull member 4, and the angle between the extension direction of the second arm 512 and the axial direction of the push-pull member 4 are each an acute angle. When the valve body 1 is detachably fixed to the fixing member 3, the end of the expandable stent 2 farther away from the valve body 1 is located outside a joint of the first arm 511 and the second arm 512. When an end of the push-pull member 4 farther away from the expansion assembly 5 moves in a direction farther away from the fixing member 3, the telescopic arm 51 of the expansion assembly 5 contracts, the angle between the first arm 511 and the second arm 512 gradually decreases, and the distance between the joint of the first arm 511 and the second arm 512 and the axis of the push-pull member 4 continuously increases, that is, the expansion assembly 5 expands outwards along the radial direction of the expandable stent 2. Therefore, the end of the expandable stent 2 farther away from the valve body 1 is capable of being expanded along the radial direction of the end of the expandable stent 2, so that the end of the expandable stent 2 farther away from the valve body 1 is capable of being supported on one side of the native valve annulus. In other embodiments, the number of telescopic arms 51 may be three or more as long as the expandable stent 2 can be expanded.

In this embodiment, limitation on the expanding structure is not limited thereto, and the expanding structure may further include a medium catheter and an inflatable balloon. The medium catheter is configured to penetrate the fixing member 3. The medium catheter includes an inner catheter and an outer catheter. The inner catheter is configured to penetrate the outer catheter and a space exists between the inner catheter and the outer catheter. The inflatable balloon is configured to penetrate the inner catheter. An end of the inflatable balloon is connected to the outer catheter, and another end of the inflatable balloon is sealedly connected to the inner catheter. An opening of an end of the outer catheter farther away from the inflatable balloon is a stepped opening, and a spring is disposed between an end of the inner catheter farther away from the inflatable balloon, and the stepped opening of the outer catheter. A medium (gas or normal saline) may be introduced into the inflatable balloon through the space between the outer catheter and the inner catheter so as to make the inflatable balloon inflate, and thus the end of the expandable stent 2 farther away from the valve body 1 is expanded along the radial direction of the end of the expandable stent 2. Moreover, during the inflation process of the inflatable balloon, the axial length of the inflatable balloon in the extension direction of the inner catheter decreases. Meanwhile, the spring is compressed until the end of the expandable stent 2 farther away from the valve body 1 is expanded to the preset position along the radial direction of the end of the expandable stent 2 by the inflatable balloon. After the medium in the inflatable balloon is withdrawn, the inflatable balloon returns to an initial state.

As shown in FIGS. 4 to 6, the implantation device further includes a valve holder 31. The valve holder 31 is detachably disposed on the fixing member 3, and the valve body 1 is detachably connected to the valve holder 31. The valve holder 31 includes a perforated connector 311 and a support arm 312. The perforated connector 311 is of a ring-shaped structure and can be sleeved on the fixing member 3. An end of the support arm 312 is connected to the perforated connector 311, and another end of the support arm 312 is connected to the valve frame 12. Moreover, the support arm 312 extends in a direction closer to the expansion assembly 5 in the axial direction of the fixing member 3. In this embodiment, in order to make the valve frame 12 be stably fixed on the valve holder 31, three support arms 312 are disposed, and the three support arms 312 are distributed at equal intervals along the periphery of the perforated connector 311. In other embodiments, four or more support arms 312 may also be disposed to improve the stable fixation of the valve body 1. In addition, the support frame 121 is sewn and fixed to the support arm 312 by suture. The polyester fabric is disposed on the support frame 12. The support frame 121 is sewn and fixed to the support arm 312 by suture through the polyester fabric, so that the support arm 312 and the valve body 1 can be conveniently separated from each other after the valve body 1 is fixed at the position of the native valve annulus.

Figure 7:
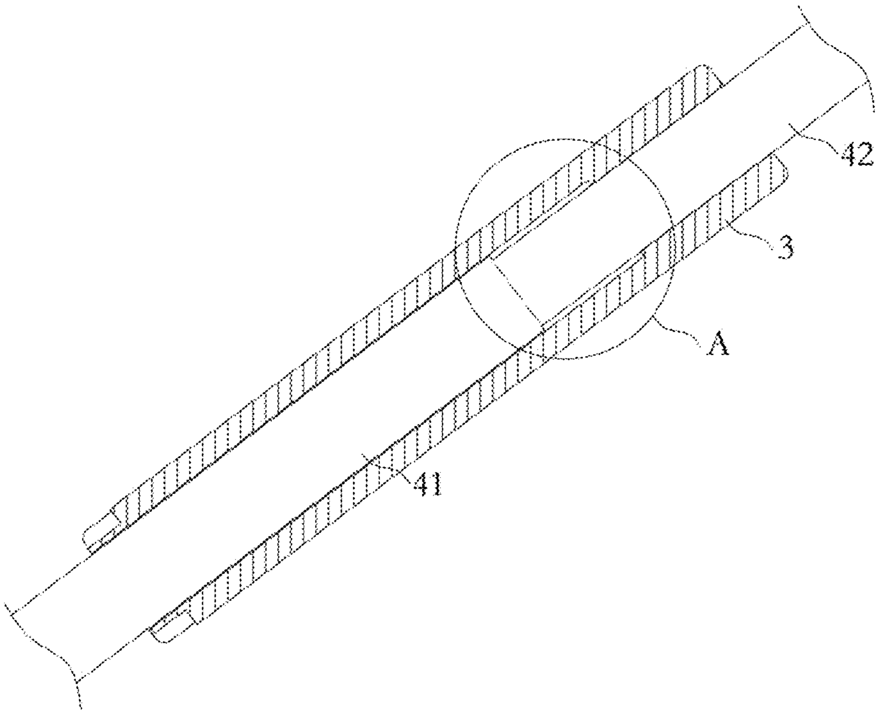
FIG. 7 is a partial sectional view of a push-pull member and a fixing member according to an embodiment of the present application.
Figure 8:
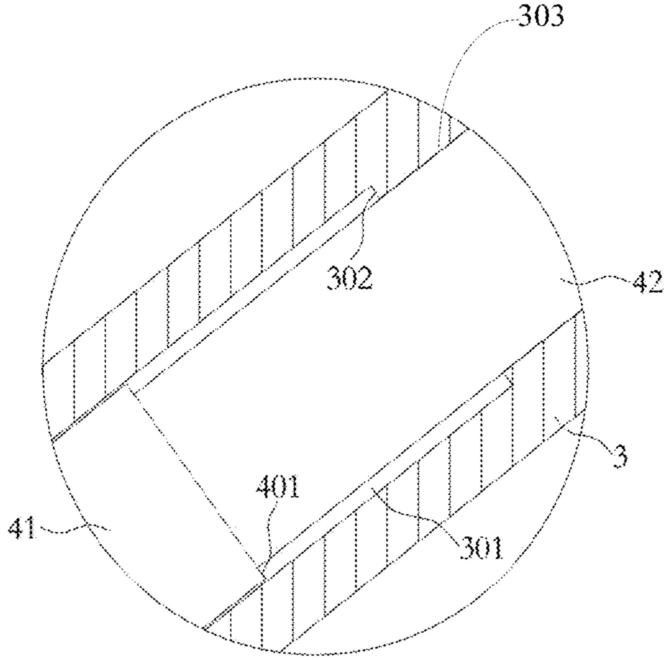
FIG. 8 is a partial enlarged view of part A of FIG. 7 according to an embodiment of the present application.

FIG. 7 is a partial sectional view of a fixing member and a push-pull member according to an embodiment of the present application; and FIG. 8 is a partial enlarged view of part A of FIG. 7 according to an embodiment of the present application. In order to ensure that the expansion assembly 5 is capable of expanding the end of the expandable stent 2 farther away from the valve body 1 along the radial direction of the end of the expandable stent 2 to the preset position under the driving of the push-pull member 4, the fixing member 3 is capable of limiting the movement of the push-pull member 4 to prevent the push-pull member 4 from moving improperly or moving too long a distance. In this embodiment, a stepped hole is disposed along the axial direction of the fixing member 3, including a first hole 301 and a second hole 303. A diameter of the first hole 301 is larger than a diameter of the second hole 303, a second stepped surface 302 is formed between the first hole 301 and the second hole 303, and the first hole 301 is closer to the expansion assembly 5 than the second hole 303. The push-pull member 4 is a stepped shaft including a first portion 41 and a second portion 42. A cross-sectional area (or diameter) of the first portion 41 is larger than a cross-sectional area (or diameter) of the second portion 42, and a first stepped surface 401 is formed between the first portion 41 and the second portion 42. The first portion 41 corresponds to the first hole 301, the second portion 42 corresponds to the second hole 303, and a joint of the first portion 41 and the second portion 42 is located in the first hole 301. An end of the first portion 41 farther away from the second portion 42 extends out of the first hole 301 and is connected to the expansion assembly 5, and an end of the second portion 42 farther away from the first portion 41 extends out of the second hole 303. Therefore, the corresponding operation on the push-pull member 4 by healthcare workers is facilitated. In the process of the second portion 42 moving away from the fixing member 3, the push-pull member 4 stops moving when the first stepped surface 401 is in contact with the second stepped surface 302. In this case, the expansion assembly 5 expands the end of the expandable stent 2 farther away from the valve body 1 along the radial direction of the end of the expandable stent 2 to the preset position.

FIG. 7 is a partial sectional view of a fixing member and a push-pull member according to an embodiment of the present application; and FIG. 8 is a partial enlarged view of part A of FIG. 7 according to an embodiment of the present application. In order to ensure that the expansion assembly 5 is capable of expanding the second end of the expandable stent 2 farther away from the valve body 1 along the radial direction of the second end of the expandable stent 2 to the preset position under the driving of the push-pull member 4, the fixing member 3 is capable of limiting the movement of the push-pull member 4 to prevent the push-pull member 4 from moving improperly or moving too long a distance. In this embodiment, a stepped hole is disposed along the axial direction of the fixing member 3, including a first hole 301 and a second hole 303. A diameter of the first hole 301 is larger than a diameter of the second hole 303, a second stepped surface 302 is formed between the first hole 301 and the second hole 303, and the first hole 301 is closer to the expansion assembly 5 than the second hole 303. The push-pull member 4 is a stepped shaft including a first portion 41 and a second portion 42. A cross-sectional area (or diameter) of the first portion 41 is larger than a cross-sectional area (or diameter) of the second portion 42, and a first stepped surface 401 is formed between the first portion 41 and the second portion 42. The first portion 41 corresponds to the first hole 301, the second portion 42 corresponds to the second hole 303, and a joint of the first portion 41 and the second portion 42 is located in the first hole 301. An end of the first portion 41 farther away from the second portion 42 extends out of the first hole 301 and is connected to the expansion assembly 5, and an end of the second portion 42 farther away from the first portion 41 extends out of the second hole 303. Therefore, the corresponding operation on the push-pull member 4 by healthcare workers is facilitated. In the process of the second portion 42 moving away from the fixing member 3, the push-pull member 4 stops moving when the first stepped surface 401 is in contact with the second stepped surface 302. In this case, the expansion assembly 5 expands the second end of the expandable stent 2 farther away from the valve body 1 along the radial direction of the second end of the expandable stent 2 to the preset position.

The operation process of the implantation device is described below.

The valve body 1 is sewn and fixed to the support arm 312 of the valve holder 31 by suture, and then the expansion assembly 5, the push-pull member 4 and the fixing member 3 pass through the hole channel formed when the three valve leaflets 122 are opened simultaneously, and the perforated connector 311 of the valve holder 31. The valve holder 31 is connected to the fixing member 3. In this case, the end of the expandable stent 2 farther away from the valve body 1 is located outside the expansion assembly 5, and each telescopic arm 51 is in an extended state, as shown in FIG. 5.

The valve body 1 is delivered to the position of the native valve annulus by the implantation device, so that the insertion hook 21 at an end of the expandable stent 2 is inserted into the native valve annulus, and the valve body 1 is initially fixed. When the end of the push-pull member 4 farther away from the expansion assembly 5 moves in a direction far away from the fixing member 3, the telescopic arm 51 of the expansion member 5 contracts, and the joint of the first arm 511 and the second arm 512 moves away from the axis of the push-pull member 4, that is, the expansion assembly 5 expands outwards along the radial direction of the expandable stent 2. Therefore, the end of the expandable stent 2 farther away from the valve body 1 is expanded to the preset position along the radial direction of the end of the expandable stent 2, so that the end of the expandable stent 2 farther away from the valve body 1 can be supported on one side of the native valve annulus, and the expansion assembly 5 remains in this state, as shown in FIG. 6.

After preset time, the end of the push-pull member 4 farther away from the expansion assembly 5 is moved in a direction close to the fixing member 3, so that the telescopic arm 51 of the expansion assembly 5 is extended, and the joint of the first arm 511 and the second arm 512 moves in a direction close to the axis of the push-pull member 4 until the joint returns to an initial position, that is, the expansion assembly 5 contracts inwards along the radial direction of the expandable stent 2. The suture between the support arm 312 and the valve body 1 is cut off, and the implantation device is taken out integrally from the hole channel formed when the three valve leaflets 122 are opened.

According to the implantation device provided in this embodiment, the valve body 1 is delivered by the implantation device to the position where the native valve annulus is located, the insertion hook 21 is inserted into the native valve annulus, the end of the expandable stent 2 farther away from the valve body 1 is expanded along the radial direction of the end of the expandable stent 2 and supported on one side of the native valve annulus, and the valve body 1 is fixed at the position of the native valve annulus from two sides of the native valve annulus. Compared with the related art, this embodiment omits the process of sewing the surgical valve to the position of the native valve annulus, and the surgical valve can be more firmly combined at the position of the native valve annulus. Therefore, the damage to the surgical valve during the sewing process can be avoided, the surgery time can be shortened, the risk of the surgery can be reduced, and the risk of the surgical valve falling off in in the human body after the surgery can also be avoided.

What is claimed is:

1. An implantation device for a surgical valve, configured to implant a surgical valve, wherein the surgical valve comprises a valve body and an expandable stent; wherein the valve body comprises a valve base and a valve frame disposed on the valve base; and the expandable stent is of a cylindrical structure with openings at a first end and a second end of the expandable stent, the first end of the expandable stent is sleeved on the valve base, the expandable stent is provided with a plurality of insertion hooks configured to be inserted into a native valve annulus and disposed along a periphery of the first end of the expandable stent, and the second end of the expandable stent is configured to be radially expanded so as to be supported on one side of the native valve annulus;

the implantation device for the surgical valve comprises a fixing member and an expanding structure, wherein the fixing member is a tubular structure and configured to detachably penetrate the valve body, and the expanding structure is configured to pass through the valve body to be located within the expandable stent and is configured to radially expand the second end of the expandable stent to a preset position;

wherein the expanding structure comprises a push-pull member, and a plurality of telescopic arms disposed along a periphery of the push-pull member;

the push-pull member penetrates through the fixing member and is movable relative to the fixing member in an axial direction of the fixing member;

each of a first end and a second end of the push-pull member extends out of the fixing member;

each of the plurality of telescopic arms comprises a first arm and a second arm which are rotatably connected to each other, an end of the first arm facing away from the second arm is rotatably connected to the first end of the push-pull member, and an end of the second arm facing away from the first arm is rotatably connected to the fixing member;

wherein the second arm has a side surface facing away from the push-pull member, the side surface of the second arm is concave and comprises a first area and a second area which are positioned at an obtuse angle to each other, a boundary line between the first area and the second area is substantially perpendicular to a length direction of the push-pull member;

when the second end of the push-pull member moves in a direction further away from the fixing member, a distance between the push-pull member and a joint of the first arm and the second arm increases;

wherein the push-pull member is a square column, and the fixing member is of a square cylindrical structure;

wherein the push-pull member is a stepped shaft, a first stepped surface facing the second end of the push-pull member is disposed along a periphery of the push-pull member, a stepped hole is disposed along an axial direction of the fixing member, a second stepped surface facing the first end of the push-pull member is disposed along a periphery of the stepped hole, and the first stepped surface and the second stepped surface are configured to limit a position of the push-pull member;

wherein the stepped shaft comprises a first portion and a second portion located closer to the first end of the push-pull member than the first portion, a cross-sectional area of the first portion is larger than a cross-sectional area of the second portion, and the first stepped surface is formed between the first portion and the second portion;

wherein the stepped hole comprises a first hole and a second hole located father from the first end of the push-pull member than the first hole, a cross-sectional area of the first hole is larger than a cross-sectional area of the second hole, the second stepped surface is formed between the first hole and the second hole.

2. The implantation device of claim 1, further comprising a valve holder, wherein the valve holder is disposed on the fixing member and the valve holder is detachably connected to the valve body.

3. The implantation device of claim 2, wherein the valve holder comprises a perforated connector and a support arm, the perforated connector is sleeved on the fixing member, a first end of the support arm is connected to the perforated connector, and a second end of the support arm is configured to be detachably connected to the valve body.

4. The implantation device of claim 1, wherein the expandable stent is of a reticular structure, and is made of metal.

5. The implantation device of claim 4, further comprising a valve holder, wherein the valve holder is disposed on the fixing member and the valve holder is detachably connected to the valve body.

6. The implantation device of claim 5, wherein the valve holder comprises a perforated connector and a support arm, the perforated connector is sleeved on the fixing member, a first end of the support arm is connected to the perforated connector, and a second end of the support arm is configured to be detachably connected to the valve body.

7. The implantation device of claim 1, wherein each of the plurality of insertion hooks is provided with a barbed structure.

* * * * *